(12) United States Patent
Freeman et al.

(10) Patent No.: US 10,238,334 B2
(45) Date of Patent: *Mar. 26, 2019

(54) ARTERIAL AND VENOUS BLOOD METRICS

(71) Applicant: ZOLL Medical Corporation, Chelmsford, MA (US)

(72) Inventors: Gary A. Freeman, Waltham, MA (US); Ulrich Herken, Medford, MA (US); Christopher L. Kaufman, Somerville, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/831,435

(22) Filed: Dec. 5, 2017

(65) Prior Publication Data
US 2018/0153468 A1    Jun. 7, 2018

Related U.S. Application Data

(63) Continuation of application No. 13/957,091, filed on Aug. 1, 2013, now Pat. No. 9,861,311.
(Continued)

(51) Int. Cl.
*A61B 5/00* (2006.01)
*A61B 5/053* (2006.01)
(Continued)

(52) U.S. Cl.
CPC .......... *A61B 5/4848* (2013.01); *A61B 5/0002* (2013.01); *A61B 5/0265* (2013.01);
(Continued)

(58) Field of Classification Search
CPC . A61B 2505/01; A61B 5/0002; A61B 5/0265; A61B 5/0295; A61B 5/0536;
(Continued)

(56) References Cited

U.S. PATENT DOCUMENTS

| 4,683,890 A | 8/1987 | Hewson |
|---|---|---|
| 5,782,774 A | 7/1998 | Shmulewitz |

(Continued)

FOREIGN PATENT DOCUMENTS

| EP | 1778083 B1 | 5/2007 |
|---|---|---|
| WO | 2006006871 A2 | 1/2006 |

OTHER PUBLICATIONS

Rass et al., Venoarterial flow index steadily improves after endovenous laser treatment of the great saphenous vein, Dermatol Surg., 36(11), Abstract.

(Continued)

*Primary Examiner* — Tiffany Weston
(74) *Attorney, Agent, or Firm* — The Webb Law Firm

(57) ABSTRACT

A medical device including a probe configured to be orally inserted into a lumen extending into the thorax of the subject, a plurality of electrodes, and a control circuit. The probe includes a first electrode. The plurality of electrodes includes at least one second electrode and at least one third electrode configured to be disposed externally on the thorax of the subject on a first side of a sternum of the subject and a second side of the sternum of the subject, respectively, the second side opposite the first side. The control circuit is electrically coupled to the first electrode and the at least one second and third electrodes and configured to measure an impedance between the first electrode and each of the at least one second and third electrodes and determine a ratio of arterial blood volume relative to venous blood volume based upon the measured impedance.

15 Claims, 6 Drawing Sheets

Related U.S. Application Data

(60) Provisional application No. 61/679,275, filed on Aug. 3, 2012, provisional application No. 61/684,435, filed on Aug. 17, 2012.

(51) Int. Cl.
*A61B 5/0265* (2006.01)
*A61B 5/0295* (2006.01)

(52) U.S. Cl.
CPC .......... *A61B 5/0295* (2013.01); *A61B 5/0536* (2013.01); *A61B 5/0538* (2013.01); *A61B 5/72* (2013.01); *A61B 5/4836* (2013.01); *A61B 2505/01* (2013.01)

(58) Field of Classification Search
CPC ... A61B 5/0538; A61B 5/4836; A61B 5/4848; A61B 5/72
See application file for complete search history.

(56) References Cited

U.S. PATENT DOCUMENTS

| | | |
|---|---|---|
| 6,351,671 B1 | 2/2002 | Myklebust et al. |
| 6,749,567 B2 | 6/2004 | Davis et al. |
| 7,308,304 B2 | 12/2007 | Hampton et al. |
| 7,720,529 B1 | 5/2010 | Schecter |
| 9,861,311 B2 * | 1/2018 | Freeman .............. A61B 5/4848 |
| 2002/0193700 A1 | 12/2002 | Bohm et al. |
| 2005/0054939 A1 | 3/2005 | Ben-Ari et al. |
| 2010/0022886 A1 | 1/2010 | Ayati et al. |
| 2012/0150169 A1 | 6/2012 | Zielinksi et al. |
| 2012/0191024 A1 | 7/2012 | Halperin et al. |

OTHER PUBLICATIONS

Edelson, The Science of CPR: Identifying the factors key to improved patient outcomes, 2010, Journal of Emergency Medical Services, Web retrieved from: http://www.jems.com/articles/2010/11/sciencecpr.html.

Abella et al., Quality of Cardiopulmonary Resuscitation During In-Hospital Cardiac Arrest, 2005, JAMA, 293(3), 305-310.

Lee, Blood vessel changes in hypertension: Structure and function, vol. II, 1989, CRC Press, p. 129.

International Search Report and Written Opinion from corresponding PCT/US2013/053253 dated Nov. 22, 2013.

* cited by examiner

ARTERIAL AND VENOUS BLOOD METRICS

CROSS REFERENCE TO RELATED APPLICATIONS

This application is a continuation of U.S. patent application Ser. No. 13/957,091 entitled "Arterial and Venous Blood Metrics", filed on Aug. 1, 2013, which claims priority under 35 U.S.C. § 119(e) to U.S. Provisional Application Ser. No. 61/679,275 entitled "Arterial and Venous Blood Metrics", filed Aug. 3, 2012, and to U.S. Provisional Application Ser. No. 61/684,435 entitled "Arterial and Venous Blood Metrics", filed Aug. 17, 2012, all of which are incorporated herein by reference in their entireties.

BACKGROUND

Embodiments of the present invention are generally directed to systems and methods of determining various metrics relating to the ratio of arterial and venous blood in the circulatory system of a subject, and more particularly to systems and methods of determining various metrics relating to the ratio of arterial and venous blood in the circulatory system of a subject as an indicator of the quality of Cardio Pulmonary Resuscitation (CPR).

SUMMARY

In accordance with an aspect of the present invention, a medical device is provided. The medical device comprises a probe that includes a first electrode and which is configured to be orally inserted into a lumen of a subject that extends into the thorax of the subject, a plurality of electrodes, and a control circuit. The plurality of electrodes includes at least one second electrode configured to be disposed externally on the thorax of the subject on a first side of a sternum of the subject and at least one third electrode configured to be disposed externally on the thorax of the subject on a second side of the sternum of the subject that is opposite the first side. The control circuit is electrically coupled to the first electrode, the at least one second electrode, and the at least one third electrode. The control circuit is configured to measure an impedance between the first electrode and each of the at least one second and third electrodes and determine a ratio of arterial blood volume relative to venous blood volume based upon the measured impedance.

In some embodiments, the control circuit is further configured to measure the impedance between the first electrode and each of the at least one second and third electrodes over a period of time, and to determine a rate of change of the ratio of the arterial blood volume relative to the venous blood volume over the period of time. In various embodiments, the control circuit is further configured to issue a recommendation to modify an intravascular fluid volume of the subject based at least in part on the determined rate of change of the ratio of the arterial blood volume relative to the venous blood volume over the period of time. In other embodiments, the control circuit is further configured to issue a recommendation to modify an intravascular fluid volume of the subject based at least in part on the determined ratio of arterial blood volume relative to venous blood volume.

In accordance with some embodiments, the control circuit is further configured to determine a ratio of the arterial blood volume relative to a capacity of the arterial blood system of the subject based upon the measured impedance, to determine a ratio of the venous blood volume relative to a capacity of the venous blood system of the subject based upon the measured impedance, or both.

In various embodiments, the control circuit is further configured to generate a metric indicative of a quality of cardio pulmonary resuscitation being performed on the subject. In some embodiments, the control circuit is further configured to issue a recommendation to modify the cardio pulmonary resuscitation being performed on the subject based on the metric. The recommendation can include at least one of varying the rate of cardio pulmonary resuscitation compressions, varying a depth of the cardio pulmonary resuscitation compressions, varying a position at which the cardio pulmonary resuscitation compressions are applied to the subject, varying a direction at which the cardio pulmonary resuscitation compressions are applied to the subject, changing a duration of time over which each compression is applied to the subject, changing a duration of time over which compressive forces are released, and recommending administration of a pharmacological compound.

In accordance with some embodiments, the medical device includes a user interface, and the control circuit is further configured to at least one of audibly and visually present the recommendation on the user interface. In various embodiments, the medical device includes a communication interface by which it can communicate with an electromechanical chest compression device, and the control circuit is further configured to communicate the recommendation to the electromechanical chest compression device. In various embodiments, the medical device can communicate via the communication interface with a resuscitation device, such as a chest compression device, a CPR coaching and feedback device, or a defibrillator.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
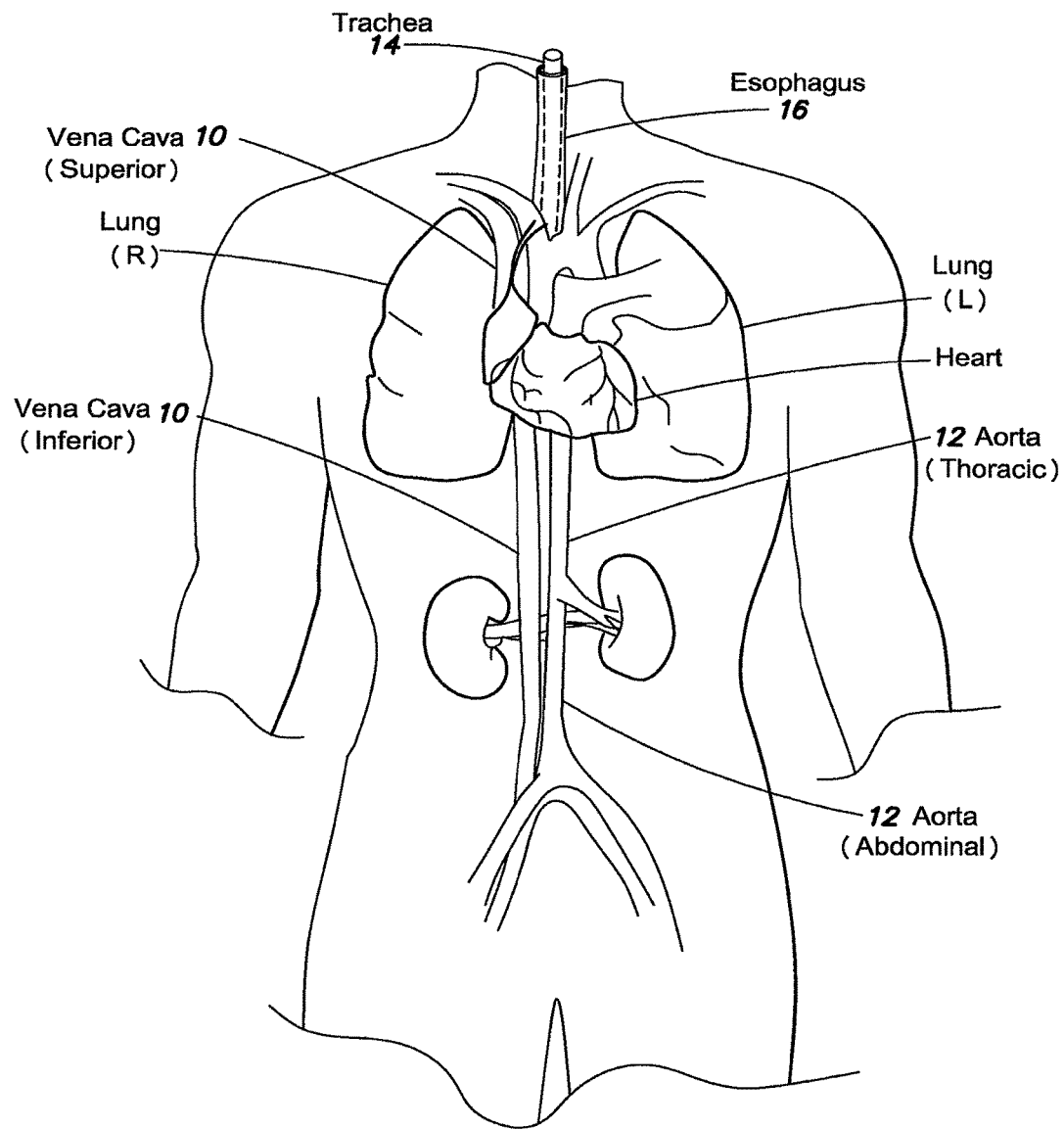
FIG. 1 illustrates the circulatory system of a human subject.

Embodiments of the invention are not limited to the details of construction and the arrangement of components set forth in the following description or illustrated in the drawings. Embodiments of the invention are capable of being practiced or of being carried out in various ways. Also, the phraseology and terminology used herein is for the purpose of description and should not be regarded as limiting. The use of "including," "comprising," or "having,"

"containing," "involving," and variations thereof herein, is meant to encompass the items listed thereafter and equivalents thereof as well as additional items.

Cardiac arrest is a major cause of death worldwide. Various resuscitation efforts aim to maintain the body's circulatory and respiratory systems during cardiac arrest in an attempt to save the life of the subject. Such resuscitation efforts may include CPR (i.e., chest compressions with or without artificial respiration). A number of different devices are commercially available to improve the effectiveness of CPR, including manually operated devices, such as the PocketCPR®. CPR coaching and feedback device, and electromechanical chest compression devices, such as the AutoPulse® Non-invasive Cardiac Support Pump, each available from ZOLL Medical Corporation, of Chelmsford, Mass.

Applicants have determined that various metrics relating to the ratio of arterial and venous blood in the circulatory system of a subject may be used an indicator of the quality of Cardio Pulmonary Resuscitation (CPR) being performed on the subject. Such metrics may include a ratio of the arterial blood volume relative to the venous blood volume at a particular instant of time, changes in the ratio of arterial blood volume relative to the venous blood volume over a period of time, the rate of filling of the arterial and venous vessels over time, changes in the rate of filling of the arterial and venous vessels over a period of time, a ratio of the capacity of arterial blood volume relative to the capacity of venous blood volume at a particular instant of time, changes in the capacity of arterial blood volume relative to the capacity of venous blood volume over a period of time, the directionality (i.e., retrograde or antegrade) of blood flow, and changes in the directionality of blood flow over a period of time.

Applicants have determined that these metrics can be indicative of the quality of CPR being performed on a subject, and further, that such metrics may be used to modify the CPR being performed on the subject to enhance the quality of the delivered CPR. Such modifications may include adjusting the location at which compressions are applied to the subject, adjusting a direction in which compressions are applied to the subject, adjusting the frequency, depth, or duration of the CPR compressions, adjusting the amount of time over which the compressive forces are released, etc.

FIG. 1 illustrates the circulatory system of human subject. As illustrated in FIG. 1, the circulatory system includes both a venous portion that includes the vena cava 10 and its associated veins and an arterial portion that includes the aorta 12 and its associated arteries. As shown in FIG. 1, both the trachea 14 and the esophagus 16 of the subject descend centrally into the subject's thorax, with the great vessels of the venous portion (e.g., the vena cava) being disposed substantially to the right of the subject's trachea or esophagus and with the great vessels of the arterial portion (e.g., the aorta) being disposed substantially to the left of the subject's trachea or esophagus.

Various metrics relating to the ratio of arterial and venous blood in the circulatory system of a subject can be indicative of the quality of CPR that is being performed on the subject. In general, during effective CPR, the relative volume of blood in the arterial portion of the subject's circulatory system should be greater than that in the venous portion. By monitoring various metrics relating to the ratio of the volume of arterial blood relative to the volume of venous blood in the circulatory system of the subject, the effectiveness of CPR can be increased and the CPR may be tailored to adjust to the individual characteristics of the subject.

In accordance with an aspect of the present invention, a medical device is provided that is capable of monitoring various metrics relating to the ratio of arterial and venous blood in the circulatory system of a subject. In accordance with one embodiment, the medical device measures the impedance of the great vessels (e.g., the aorta and the vena cava) to determine a ratio of the arterial blood volume relative to the venous blood volume at a particular instant of time, changes in the ratio of arterial blood volume relative to the venous blood volume over a period of time, the rate of filling of the arterial and venous vessels over time, changes in the rate of filling of the arterial and venous vessels over a period of time, a ratio of the capacity of arterial blood volume relative to the capacity of venous blood volume at a particular instant of time, and changes in the capacity of arterial blood volume relative to the capacity of venous blood volume over a period of time. In some embodiments, the medical device may be capable of also determining the directionality of blood flow and changes in the directionality of blood flow over a period of time. Although aspects and embodiments of the present invention are primarily directed to the use of impedance measurements to determine the various metrics, those skilled in the art should appreciate that other types of measurements may alternatively or additionally be used, such as ultrasound.

Figure 2:
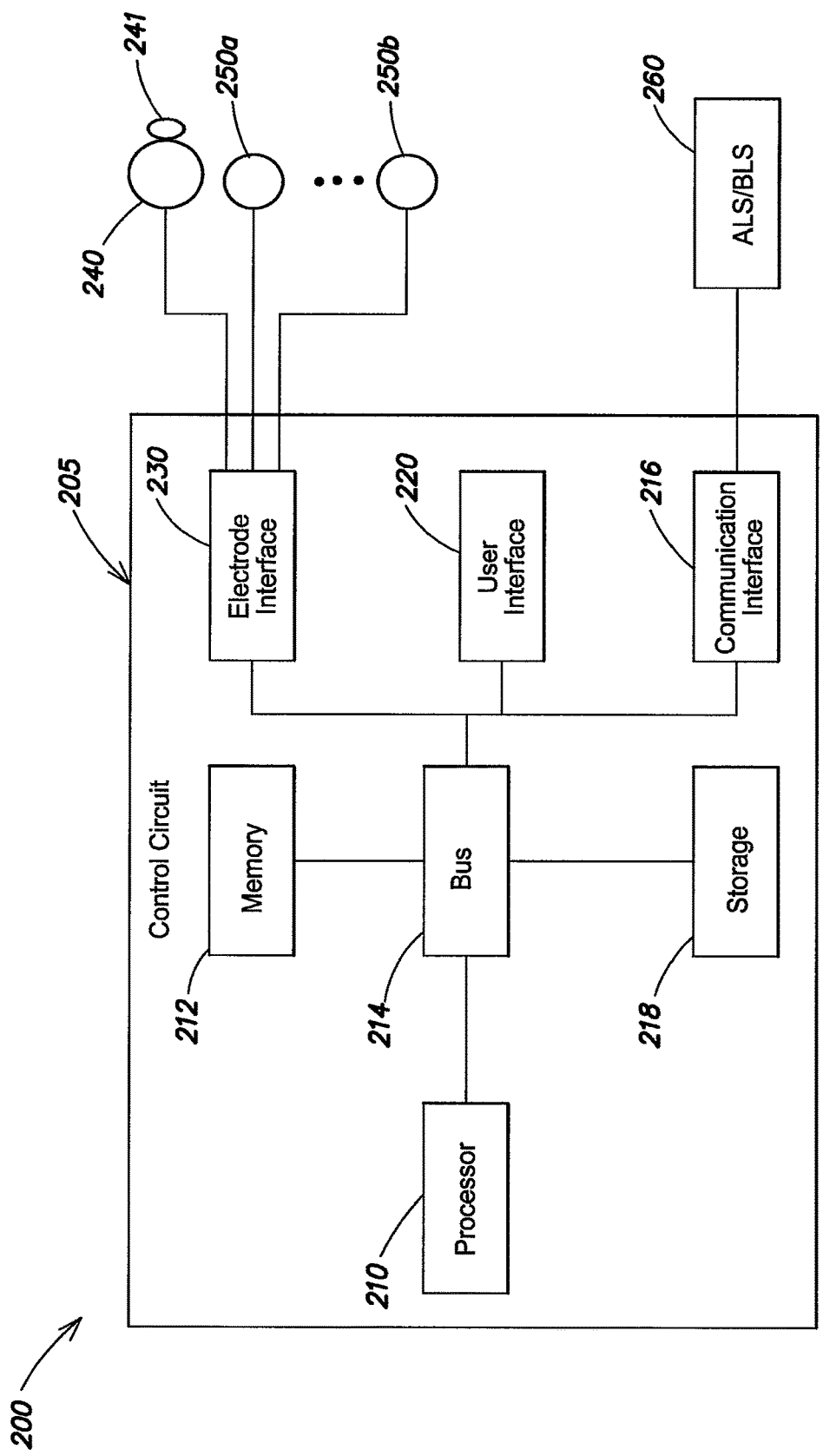
FIG. 2 illustrates a medical device that may be used to monitor the thoracic impedance of a subject and to determine various metrics relating to the ratio of arterial and venous blood in the circulatory system of the subject in accordance with an embodiment of the present invention.

As shown in FIG. 2, the medical device 200 includes a control circuit 205 that is electrically coupled to a probe 240 that includes at least one first electrode 241 and a plurality of additional electrodes 250 including at least one second electrode 250a, and at least one third electrode 250b. As described in more detail with respect to FIGS. 3 and 4 below, the probe 240 is configured to be orally inserted into a lumen of the subject, such as the trachea or the esophagus of the subject, and the plurality of additional electrodes 250 are configured to be disposed externally on the thorax of the subject.

As shown in FIG. 2, the control circuit 205 may be implemented on a computer system, such as a personal computer or workstation. It should be appreciated that embodiments of the present invention are not limited to executing on any particular type of computer system, as various aspects of the present invention may be implemented in software, hardware or firmware, or any combination thereof, including specially-programmed hardware and/or software.

As depicted, the control circuit 205 includes a processor 210, a memory 212, a bus 214, a communication interface 216, a user interface 220, an electrode interface 230 and a storage system 218. The processor 210, which may include one or more microprocessors or other types of controllers, can perform a series of instructions that manipulate data, including data provided by the electrodes 241, 250a, and 250b. The processor 210 may be a well-known, commercially available processor such as an Intel Pentium, Intel Atom, ARM Processor, Motorola PowerPC, SGI MIPS, Sun UltraSPARC, or Hewlett-Packard PA-RISC processor, or may be any other type of processor or controller as many other processors and controllers are available. The processor 210 may execute an operating system which may be, among others, a Windows-based operating system (for example, Windows NT, Windows 2000/ME, Windows XP, Windows 7, or Windows Vista) available from the Microsoft Corporation, a MAC OS System X operating system available from Apple Computer, one of many Linux-based operating system distributions (for example, the Enterprise Linux operating system available from Red Hat Inc.), a Solaris operating system available from Sun Microsystems, or a UNIX operating systems available from various sources. Many other operating systems may be used, and embodiments are not limited to any particular operating system.

The processor and operating system together define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, functions in accord with aspects of the present invention may be implemented using an object-oriented programming language, such as SmallTalk, JAVA, C++, Ada, or C# (C-Sharp). Other object-oriented programming languages may also be used. Alternatively, procedural, scripting, or logical programming languages may be used.

As shown, the processor 210 is connected to the other control circuit components, including the memory 212, the storage system 218, and the interfaces 216, 220, and 230, by the bus 214. The memory 212 may be used for storing programs and data during operation of the control circuit 205. Thus, the memory 212 may be a relatively high performance, volatile, random access memory such as a dynamic random access memory (DRAM) or static memory (SRAM). However, the memory 212 may include any device for storing data, such as a disk drive or other non-volatile storage device, such as flash memory or phase-change memory (PCM). Various embodiments in accord with the present invention can organize the memory 212 into particularized and, in some cases, unique structures to perform the aspects and functions disclosed herein.

The various components of the control circuit 205 are coupled to one another by an interconnection element such as the bus 214. The bus 214 may include one or more physical busses (for example, busses between components that are integrated within a same machine), and may include any communication coupling between control circuit components including specialized or standard computing bus technologies such as IDE, SCSI, PCI and InfiniBand. Thus, the bus 214 enables communications (for example, data and instructions) to be exchanged between the various components of the control circuit 205.

The control circuit 205 also includes a number of interfaces including a communication interface 216, a user interface 220, and an electrode interface 230. The control circuit 205 may communicate with another device 260, such as an electromechanical chest compression device, a Basic Life Support (BLS) device, or an Advanced Life Support (ALS) device, such as the AED Pro or AED Plus defibrillator, LifeVest® ProPack M. D., X Series defibrillators, M Series defibrillators, R Series defibrillator BLS, or E Series defibrillator manufactured by the ZOLL Medical Corporation of Chelmsford Mass. via the communication interface 216. As described more fully below, where the device 260 is capable of providing CPR to a subject, the control circuit 205 may instruct the other device 260 to vary the CPR protocol being delivered to the subject based on the various metrics. Alternatively, where the other device 260 is an ALS device, the control circuit 205 may provide data and/or the various metrics to the other device for storage or display, or to enable the other device to guide or provide feedback to a rescuer based on the provided data or metrics.

According to a variety of examples, the communications interface 216 may support a variety of standards and protocols, examples of which include USB, TCP/IP, Ethernet, Wireless Ethernet, Bluetooth, ZigBee, M-Bus, IP, IPV6, UDP, DTN, HTTP, FTP, SNMP, CDMA, NMEA and GSM. To ensure data transfer is secure, in some examples, the control circuit 205 can transmit data via the communication interface 216 using a variety of security measures including, for example, TSL, SSL or VPN. In other examples, the communication interface 216 includes both a physical interface configured for wireless communication and a physical interface configured for wired communication.

The user interface 220 includes a combination of hardware and software components that allow the control circuit 205 to communicate with an external entity, such as a user. These components are configured to receive information from actions such as physical movement, verbal intonation or thought processes. In addition, the components of the user interface 220 can provide information to external entities. Examples of the components that may be employed within the user interface 220 include keyboards, mouse devices, trackballs, microphones, touch screens, printing devices, display screens and speakers. For example, the user interface 220 may be used to visually or audibly present a metric to a user relating to the effectiveness of the CPR being delivered, or to provide instructions as to how the CPR should be varied to increase the effectiveness of the CPR.

The electrode interface 230 is configured to receive electrical signals monitored by the various electrodes 241, 250a, 250b and to provide those electrical signals to the processor 210. The electrode interface 230 may include selection circuitry, such as a multiplexer, to select from among the different pairings of electrodes and to provide electrical signals to the processor. The electrode interface 230 may also include a plurality of differential amplifiers to receive, buffer, filter, and amplify the electrical signals provided by the different pairings of electrodes, and one or more Analog-to-Digital (A/D) converters to convert the received analog signals to a digital signal that is provided to the processor 210.

Storage system 218 may include a computer-readable and computer-writeable nonvolatile storage medium in which instructions are stored that define a program to be executed by the processor. Such a program executed by the processor may include instructions to calculate a ratio of arterial blood volume and venous blood volume at a particular instant of time, or over a period of time. The storage system 218 also may include information that is recorded, on or in, the medium, and this information may be processed by the processor 210. More specifically, the information may be stored in one or more data structures specifically configured to conserve storage space or increase data exchange performance. The instructions may be persistently stored as encoded signals, and the instructions may cause the processor to perform any of the functions described herein. A medium that can be used with various embodiments may include, for example, optical disk, magnetic disk or flash memory, among others. In operation, the processor 210 may cause data to be read from the nonvolatile recording medium into another memory, such as the memory 212, that allows for faster access to the information by the processor 210 than does the storage medium included in the storage system 218. The processor 210 may manipulate the data within the memory 212, and then copy the data to the medium associated with the storage system 218 after processing is completed. A variety of components may manage data movement between the medium and the memory 212, and the invention is not limited thereto.

Figure 3:
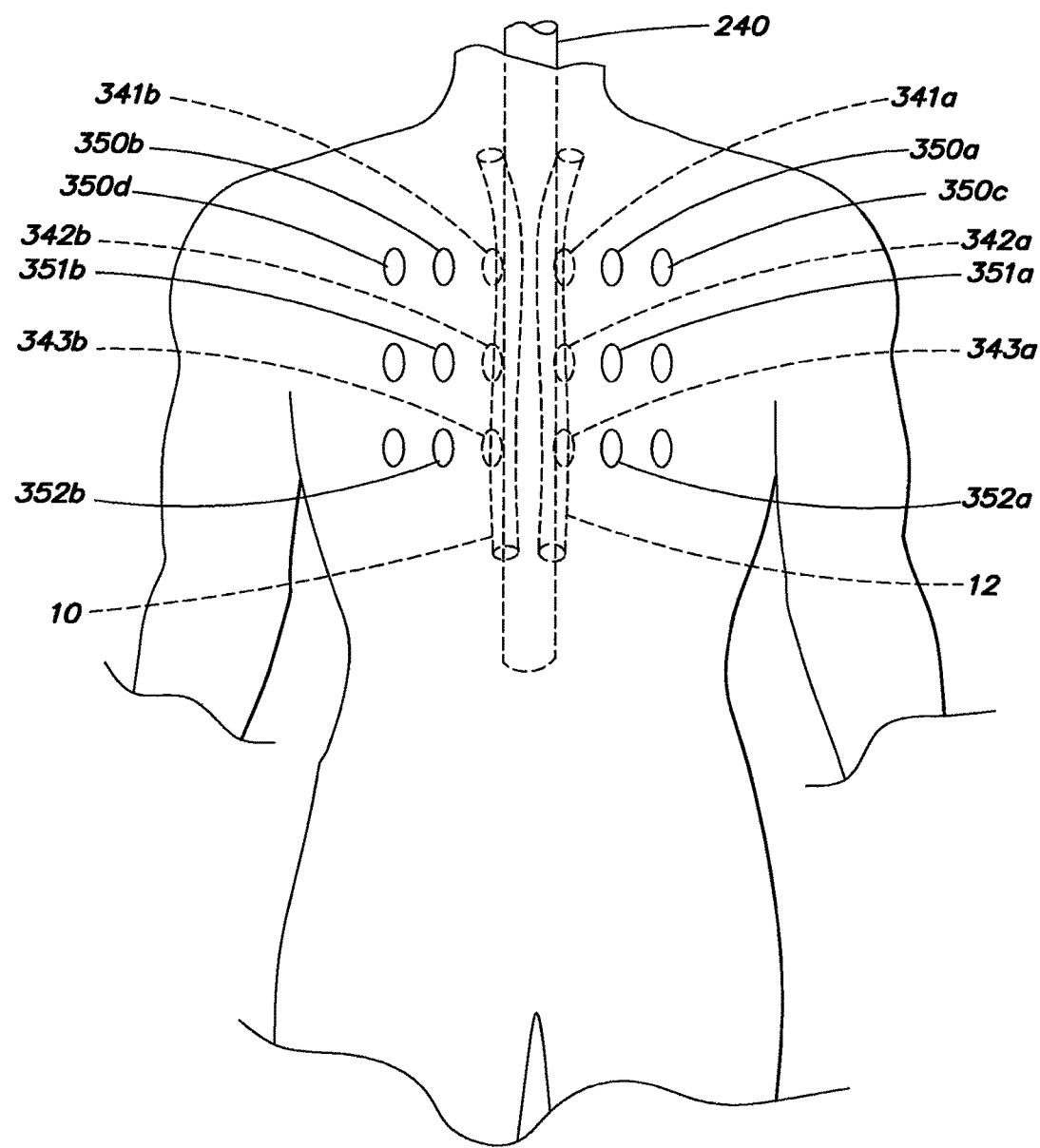
FIG. 3 illustrates a portion of the medical device of FIG. 2 that includes a probe and a plurality of external electrodes in accordance with an embodiment of the present invention.

FIG. 3 illustrates a portion of the medical device of FIG. 2 in which the probe 240 is inserted into a lumen of the subject and the plurality of additional electrodes are disposed externally on the thorax of the subject. As described with respect to FIG. 2, the probe includes at least one first electrode, and the plurality of additional electrodes includes at least one first electrode and at least one second electrode. In the embodiment illustrated in FIG. 3, the probe 240 includes a plurality electrodes 341a and 341b, 342a and 342b, and 343a and 343b disposed at spaced apart positions along a length of the probe 240. The electrodes 341, 342, 343 may be any type of electrode suitable for use inside the body of a subject, and may be mounted to an external surface of the probe 240, or integrated therein. It should be appreciated that rather than including pairs of electrodes (e.g., 341a, 341b) disposed on opposing side surfaces of the probe 240, only a single electrode (e.g., 341a, 342a, 343a) may be provided at each level along the length of the probe 240, and that in certain embodiments, only a single electrode (e.g., 342a) may be provided. However, the use of multiple electrodes disposed in spaced apart positions along the length of the probe permits impedance measurements to be made in multiple axes.

As shown in FIG. 3, the plurality of additional electrodes includes at least one second electrode 350a disposed externally on the thorax of the subject on a first side of the sternum of the subject and at least one third electrode 350b disposed externally on the thorax of the subject on a second side of the sternum of the subject that is opposite the first side. The placement of the at least one second electrode 350a and the at least one third electrode 350b permits impedance measurements of the arterial circulatory system and the venous circulatory system. The plurality of additional electrodes 350, 351, 352 may be any type of electrode suitable for external use on the body of the subject, such as wet or dry self-adhesive medical electrodes typically used to measure electrical signals on the body of a subject.

As illustrated in FIG. 3, the plurality of additional electrodes may further include additional electrodes disposed along the length and width of the thorax of the subject. For example, as shown in FIG. 3, the plurality of additional electrodes may include electrodes 350a and 350c and 350b and 350d disposed at spaced apart positions along a length of the subject's thorax to the left and right of the subject's sternum, and additional pairings of electrodes (e.g., 351a, 35b) disposed at a different position along the length of the subject's thorax to the left and right of the subject's sternum. As would be appreciated by those skilled in the art, the presence of multiple electrodes at different spaced apart positions along the length and width of the subject's thorax permits impedance measurements to be made in multiple axes.

Figure 4:
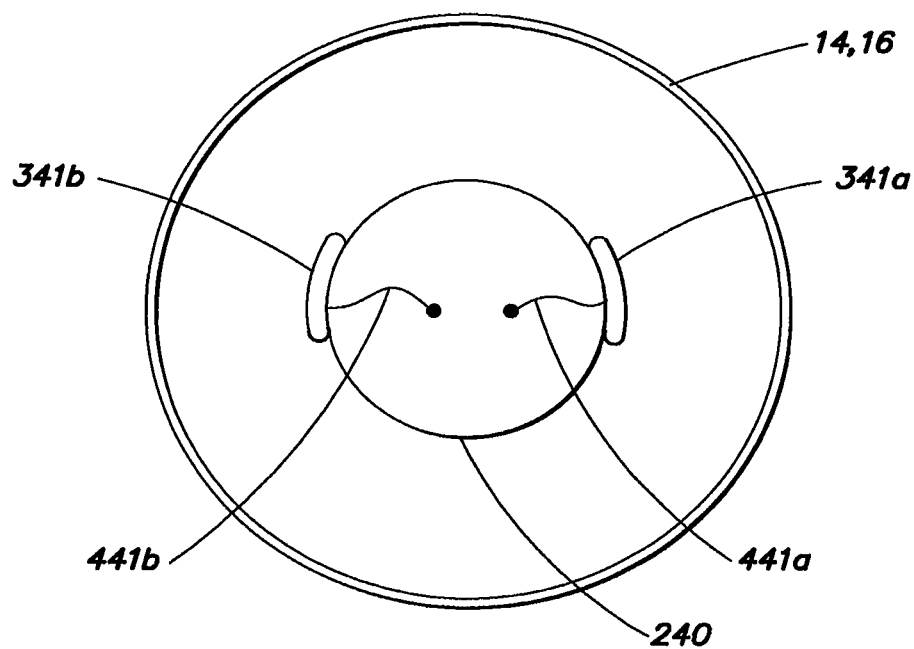
FIG. 4 is a plan view of the probe of FIG. 3.

FIG. 4 is a plan view of the probe 240 inserted into a lumen 14, 16 of a subject. The probe 240 includes at least one first electrode, and in the embodiment depicted, the probe 240 includes a pair of electrodes 341a, 341b disposed at opposing positions along the length of the probe. As noted above, the probe 240 may include only a single electrode (e.g., 341a), or alternatively may include multiple electrodes at various positions along the length of the probe. As illustrated in FIG. 4, conductive leads 441a, 441b are electrically connected to each electrode 341a, 341b, and may be routed from each electrode to the interior of the probe 240 for ease of insertion and removal of the probe 240, and for the comfort of the subject.

In use, the probe 240 is inserted into a lumen of the subject either prior to or during the performance of CPR. The probe may be inserted into either the trachea of the subject, or into the esophagus of the subject, each of which is centrally located with the body of the subject, such that the arterial and venous portions of the circulatory system of the subject are disposed predominantly to the left and right of the probe. Preferably the probe is made from a medical grade plastic or other suitable material that sufficiently rigid to permit insertion into a lumen of the subject, but which can flex during application of the compressive forces of CPR. The plurality of additional electrodes 350, 351, 352, which may be self-adhesive wet electrodes, may be attached to the skin of the subject's thorax in a well-known manner.

The at least one first electrode 341, 342, 343 of the probe 240 and the plurality of additional electrodes 350, 351, 352 are electrically coupled to the electrode interface 230 (FIG. 2), and the impedance between different pairings of the electrodes is measured. Various impedance measurements may be made using the at least one first electrode 341, 342, 343 as a source electrode and using the plurality of additional electrodes 350, 351, 352 as receiving electrodes, or vice versa. For a particular impedance measurement, the at least one first electrode 341, 342, 343 of the probe may be used as a source electrode, and in another impedance measurement, the at least one first electrode may be used as a receiving electrode. For example, and with reference to FIG. 3, electrode 341a may be paired with electrode 350a to determine the impedance of the arterial vessels, and electrode 341a may be paired with electrode 350b to determine the impedance of the venous vessels. Where multiple additional electrodes are disposed at varying positions along the width and length of the subject's thorax, full impedance tomography may be performed and used to determine the directionality of blood flow and changes in the directionality of blood flow over time.

During the performance of CPR, the impedance between various pairings of electrodes is monitored and recorded and used to determine various metrics relating to the ratio of arterial and venous blood in the circulatory system of the subject. Such metrics may include the ratio of the arterial blood volume relative to the venous blood volume at a particular instant of time as well as changes in the ratio of arterial blood volume relative to the venous blood volume over a period of time, for example, over successive 10 second intervals of time, over over-lapping sliding windows of time, or over the entire duration of CPR. Other metrics that may be determined can include the rate of filling of the arterial and venous vessels over a short period of time (e.g. 0.1-2 seconds), changes in the rate of filling of the arterial and venous vessels over successive periods of time period of time, a ratio of the capacity of arterial blood volume relative to the capacity of venous blood volume at a particular instant of time, changes in the capacity of arterial blood volume relative to the capacity of venous blood volume over a period of time, the directionality of blood flow, and changes in the directionality of blood flow over a period of time. Such metrics can be indicative of the quality of CPR being performed on a subject, and further, such metrics may be used to modify the CPR being performed on the subject to enhance the quality of the delivered CPR.

For example, if the metrics indicate that the ratio of the arterial blood volume relative to the venous blood volume is low, the depth of the CPR compressions may be increased, or the time between compressions may be increased. The device may also recommend a shift in the optimal location of the compression zone of the hands (where the CPR is being performed manually) or electromechanical compression device. For instance, it may be recommended to shift the location of the hands or compression device to the subject's left hand side, just lateral to the sternum, where the hands or compression device will be placed more directly over the heart and arterial great vessels. Where the control circuit of the medical device is capable of communicating with another device, such as an electromechanical chest compression device, instructions may be sent to the other device to modify the depth or time between CPR compressions. Alternatively, where the ratio of the arterial blood volume relative to the venous blood volume is low, the control circuit of the medical device may send instructions to the other device to modify the location at which compressions are applied to the subject, or to modify the direction at which compressions are applied to the subject to direct more blood to the arterial vessels. Where the metrics indicate that the arterial and venous blood vessels fill relatively quickly with blood during the release phase of CPR compressions, the control circuit may instruct the other device to increase the rate (i.e., frequency) at which CPR compressions are applied, and where the metrics indicate that the arterial and venous blood vessels fill relatively slowly with blood during the release phase of CPR compressions, the control circuit may instruct the other device to decrease the rate at which CPR compressions are applied.

Where CPR compressions are being performed manually, with the aid of a CPR coaching and feedback device, or with an electromechanical chest compression device, the control circuit of the medical device may visually, audibly, or both visually and audibly present instructions for modifying the CPR being performed on the subject. For example, the control circuit of the medical device may present instructions to modify the depth and/or rate of CPR compressions, to shift the location at which compressions are applied to the subject, etc. Such instructions may even include a recommendation for the administration of a pharmacological agent, such as a metabolite or metabolic enhancement agent, such as epinephrine. Alternatively, the control circuit of the medical device may communicate blood volume and flow data, or the various metrics to another device for storage or display, or to enable the other device to monitor the quality of CPR being performed, or to provide feedback or guidance to a rescuer. For example, where the other device is an ALS defibrillator, the ALS defibrillator may store the data and metrics to provide feedback to the rescuer during the performance of CPR, or to permit a rescuer to later review information to better understand how they performed with respect to the quality of CPR provided.

In an embodiment, the control circuit is configured to issue a recommendation to modify a subject's intravascular fluid volume based at least in part on at least one of the determination of the ratio of arterial blood volume relative to venous blood volume and the determination of the rate of change of the ratio of the arterial blood volume relative to the venous blood volume over the period of time. The modification may provide for an increase or a reduction in the intravascular fluid volume. In an embodiment, a user such as a nurse or a physician receiving the recommendation may provide fluid to the subject, for example, intravenously. The provision of fluid intravenously may be provided through a venous access point, for example. The fluid provided may be any fluid such as but not limited to saline, crystalloid plasma volume expanders (ringer lactate, glucose), colloidal plasma volume expanders (albumin, hydroxyethyl starch, gelatin-based fluid), oxygen enriched blood, artificial blood products, therapeutic agents and/or the like.

Figure 5:
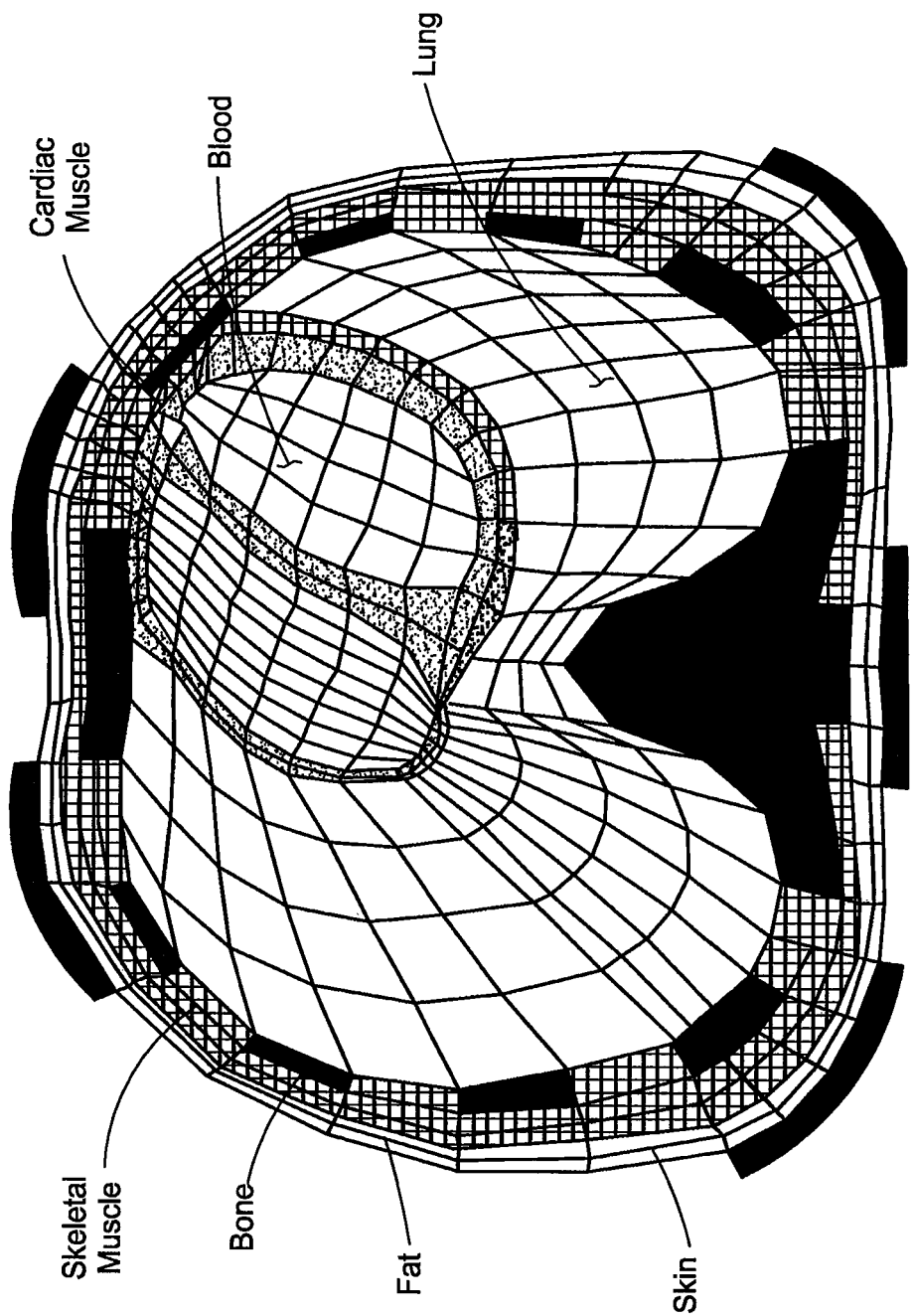
FIG. 5 is a tomography map of the electrical impedance of various tissues of a human body.

FIG. 5 is a tomographic map of the electrical impedance of various tissues of a human body. The conductances of the various tissues shown in FIG. 5 are approximately as follows:

| Tissue Type | Conductivity (ohms-cm) |
|---|---|
| Skin | 3.4 |
| Blood | 6.5 |
| Lung | 0.7 |
| Skeletal Muscle | 1.5 (transverse) |
|  | 4.2 (longitudinal) |
| Fat | 0.5 |
| Cardiac Muscle | 7.6 |
| Bone | 0.06 |

Figure 6:
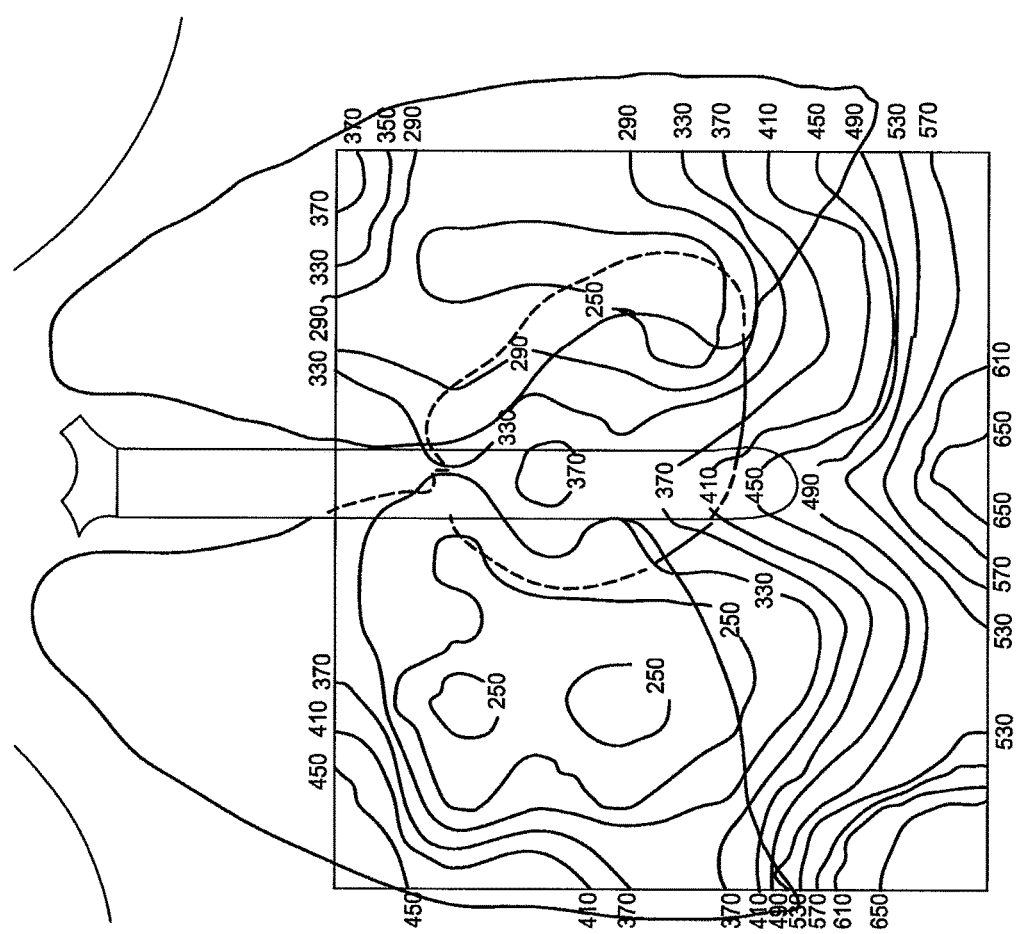
FIG. 6 is vertical cross-sectional view of the conductance of various internal organs, tissues, muscles, and bones of a human body.

Conductivities of the various tissues can vary by as much as a factor of 100. As can be seen in the isoadmittance curves shown in FIG. 6, the conductances of the internal organs, muscle and bone vary significantly, much more so than do conductances at the body surface. In accordance with one embodiment of the present invention, electrical impedance tomography (EIT) is used to determine these internal conductances or impedances. In this embodiment, electrical impedance tomography (EIT) is used to determine the resistivity distribution of the thorax in at least two dimensions, and the calculated resistivity distribution is then used to determine more accurately the relative volumes of the venous and arterial great vessels, e.g. the vena cava and aorta.

In the most basic implementation, only three electrodes with three possible electrode pairs is sufficient to use EIT methods to determine more accurately the relative volumes of the venous and arterial great vessels. At least one electrode is placed in the thorax of the subject (tracheal or esophageal probe) with two electrodes placed externally on the thorax at about the level of the sternal notch, approximately three inches to the left and right of the sternal midline. In one implementation, seven electrodes are used (three internal and four external, two on each side of the sternum, for a total of 5040 (7!) possible electrode pairs. This number is chosen for ease of implementation and cost; and other implementations with more electrode pairs are possible. For instance, three rows of electrodes may be applied to the thorax so that a full three dimensional tomographic impedance map can be calculated. This may become important as the relative location of the great vessels, in particular the aorta, shift with respect to the esophagus and trachea as they descend in the thoracic space toward the diaphragm.

The EIT system is governed by Poisson's equation:

$$\Delta \cdot \rho^{-1} \Delta V = I,$$

Where V is the voltage, $\rho$ is the resistivity distribution and I is the impressed current source distributions within the region being studied and the boundary conditions are $V_0$ and $J_0$. In the case of EIT, high frequency, low amplitude signals, e.g., 60 KHz and ~1 microampere respectively, are used. Since there are no current sources of this frequency in the body, then $\rho=0$, and Poisson's equation becomes Laplace's equation:

$$\Delta \cdot \rho^{-1} \Delta V = 0$$

In the field of EIT, several types of problems are studied:
1. The "forward problem", where $\rho$, $V_0$ and $J_0$ are given and the goal is to determine the voltage and current distributions V and J.
2. The "inverse problem", where V and J are given and the goal is to determine $\rho$.
3. The "boundary value" problem where $V_0$ and $J_0$ are given and the goal is to determine $\rho$, V and J.

In one implementation, $\rho$, V and J are determined using boundary value problem methods, then once $\rho$ is determined, the relative or absolute volumes of the venous and arterial great vessels is determined In general principle, the process of EIT involves injecting a current by an electrode, and the induced voltage is measured at multiple points on the body surface.

In accordance with one implementation, what is termed the "multireference method" is used for configuring the current voltage pairs. (Hua P, Webster J G, Tompkins W J 1987 Effect of the Measurement Method on Noise Handling and Image Quality of EIT Imaging, Proc. Annu. Int. Conf. IEEE Engineering in Medicine and Biology Society 9 1429-1430.) In the multireference method, one electrode is used as the reference electrode while the remaining electrodes are current sources with the induced voltages being measured on each electrode simultaneously while the current is being delivered. The amplitude of the current sources are individually varied and each electrode is treated as a reference lead in succession. Finite element methods are then used to convert the calculus problem ($\Delta \cdot \rho^{-1} \Delta V = 0$) into a linear algebra problem of the form YV=C, where Y, V, and C are the conductance, voltage, and current matrices respectively. Y, V, and C are also sometimes known as the master matrix, node voltage vector, and node current vector respectively. Mesh generation is performed on the two or three-dimensional physical model with triangular or quadrilateral elements for two dimensional problems and hexahedral shapes for three-dimensional problems. Boundary conditions are then set such as at the reference node or driving electrodes for Dirichlet (known surface voltages) or Neuman (known surface currents) boundary conditions. A number of methods have been used to compute the master matrix such as Gaussian elimination or Cholesky factorization.

The Newton-Raphson algorithm may also be used for reconstruction of the resistivity distribution. The algorithm is an iterative algorithm particularly well suited to non-linear problems. The Newton-Raphson method minimizes an error termed the "objective function". Here, it is defined as the equally weighted mean square difference between the measured and estimated voltage responses:

$$\Phi(\rho) = (\tfrac{1}{2})(V_e(\rho) - V_0)^T (V_e(\rho) - V_0).$$

Using methods known to those skilled in the art, an algorithm is utilized whereby a distribution is first estimated, then the theoretical voltage response to a given current input is calculated using the finite element method. The estimated voltages are subtracted from the measured voltages to obtain the objective function. If the objective function is less than an error threshold, the estimated distribution is deemed to be an acceptable estimation. If not, the following equation is used to update the resistivity distribution:

$$\Delta \rho^k = -[V_e'(\rho^k)^T V_e'(\rho^k)]^{-1} \{V_e'(\rho^k)^T [V_e'(\rho^k) - V_0]\}$$

This sequence is repeated until an acceptable estimation is achieved.

In accordance with one implementation, a table lookup method is provided to determine the estimated voltage matrix $V_e(\rho)$. The table values are based on average patient resistivity distributions and assuming correct placement of the electrode. Better accuracy can be achieved by providing anatomical markings on the electrode pads, such as using the sternal notch to provide accurate lateral and vertical positioning relative to the diaphragm.

Accuracy may also be improved by providing a secondary imaging method such as ultrasound to take advantage of its higher imaging resolution to calculate the positions of the internal organs relative to the electrodes. If a secondary imaging method such as ultrasound is used to determine the positions of internal tissues, EIT can be used to determine the resistivities of each tissue type.

In other implementations, an average resistivity value is determined for the tissue regions as defined by the secondary imaging method. This is accomplished by first defining a tissue region such as the lungs or myocardium by standard image processing methods. Next, the calculated resistivity distribution is overlayed onto the secondary image. All nodes of the resistivity distribution that are contained within a particular tissue region are combined together into a single resistivity measure for that tissue region. The method of combination may be an averaging, median, or other statistical or image processing method.

To further improve tomographic mapping accuracy additional electrodes may be placed on the thorax, in particular towards the patient's posterior.

In another implementation, a physiological parameter, e.g., the electrocardiograph (ECG), is measured in conjunction with the EIT image to determine if the electrical activity of the heart is causing blood flow in the vessels, particularly on the arterial side. In this way return of spontaneous circulation can be distinguished from pulseless electrical activity during CPR.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

The invention claimed is:
1. A medical device system comprising:
  a probe configured to be orally inserted into a lumen of a subject and configured to extend into a thorax of the subject, the probe including at least one internal electrode:
  a plurality of external electrodes including:
    a first external electrode configured to be disposed externally on the thorax of the subject on a first side of the sternum of the subject, and
    a second external electrode configured to be disposed externally on the thorax of the subject on a second side of the sternum of the subject that opposes the first side;
  a control circuit, electrically coupled to the at least one internal electrode, the first external electrode, and the second external electrode; and
  a feedback device operatively coupled to the control circuit,
  wherein the control circuit is configured to:
    measure impedance values between the at least one internal electrode and each of the first external electrode and the second external electrode;
    generate a tomographic map of the measured impedance values; and provide a feedback signal via the feedback device to provide blood volume information to a user based on the tomographic map.

2. The medical device system of claim 1, wherein the blood volume information is a ratio of arterial blood volume relative to venous blood volume in a circulatory system of the subject.

3. The medical device system of claim 2, wherein the ratio of arterial blood volume relative to venous blood volume is indicative of the quality of cardiopulmonary resuscitation being performed on the subject.

4. The medical device system of claim 2, wherein the control circuit is further configured to generate at least one metric relating to the ratio of arterial blood volume relative to venous blood volume in the circulatory system of the subject.

5. The medical device system of claim 4, wherein the at least one metric relating to the ratio of arterial and venous blood in the circulatory system of the subject comprises at least one of a ratio of arterial blood volume relative to venous blood volume at a particular instant in time, the ratio of arterial blood volume relative to the venous blood volume over a period of time, a rate of filling of arterial and venous vessels over a short period of time, changes in the rate of filling of the arterial and venous vessels over successive periods of time, a ratio of a capacity of arterial blood volume relative to a capacity of venous blood volume at a particular instant of time, changes in the capacity of arterial blood volume relative to the capacity of venous blood volume over a period of time, a directionality of blood flow, and changes in the directionality of blood flow over a period of time.

6. The medical device system of claim 1, wherein the blood volume information is a relative volume of blood of an venous great vessel and a relative volume of blood of an arterial great vessel of the subject.

7. The medical device system of claim 6, wherein the relative volume of blood of the arterial great vessel being greater than the relative volume of blood of the venous great vessel is indicative of effective cardiopulmonary resuscitation being performed on the subject.

8. The medical device system of claim 1, wherein the feedback device visually displays the blood volume information on a display device.

9. The medical device system of claim 1, wherein the control circuit is further configured to:
estimate a metric relating to a ratio of arterial and venous blood in a circulatory system of the subject based upon the tomographic map of the measured impedance values; and
provide a cardiopulmonary resuscitation feedback signal via the feedback device to modify cardiopulmonary resuscitation being performed on the subject based on the metric.

10. The medical device system of claim 9, wherein the cardiopulmonary resuscitation feedback signal comprises a recommendation that includes at least one of varying a rate of cardiopulmonary resuscitation compressions, varying a depth of the cardiopulmonary resuscitation compressions, varying a position at which the cardiopulmonary resuscitation compressions are applied to the subject, varying a direction at which the cardiopulmonary resuscitation compressions are applied to the subject, changing a duration of time over which each compression is applied to the subject, changing a duration of time over which compressive forces are released, and recommending administration of a pharmacological compound.

11. The medical device system of claim 9, wherein the metric relating to a ratio of arterial and venous blood in a circulatory system of the subject is estimated from the tomographic map by determining a resistivity distribution of the thorax of the patient in at least two dimensions using the tomographic map and estimating the metric relating to a ratio of arterial and venous blood in a circulatory system of the subject from the resistivity distribution.

12. The medical device system of claim 9, wherein further comprising a communication interface by which the medical device system can communicate with an electromechanical chest compression device, and wherein the control circuit is further configured to communicate the cardiopulmonary resuscitation feedback signal to the electromechanical chest compression device.

13. The medical device system of claim 12, wherein the cardiopulmonary resuscitation feedback signal comprises instructions to at least one of: vary a rate of cardiopulmonary resuscitation compressions, vary a depth of the cardiopulmonary resuscitation compressions, vary a position at which the cardiopulmonary resuscitation compressions are applied to the subject, vary a direction at which the cardiopulmonary resuscitation compressions are applied to the subject, change a duration of time over which each compression is applied to the subject, and change a duration of time over which compressive forces are released.

14. The medical device system of claim 9, wherein the control circuit is further configured to issue a recommendation to modify an intravascular fluid volume of the subject based at least in part on the determined metric relating to the ratio of arterial and venous blood in the circulatory system of the subject.

15. The medical device system of claim 1, further comprising a communication interface by which the medical device system can communicate with a resuscitation device, the resuscitation device including at least one of a chest compression device, a CPR coaching and feedback device, and a defibrillator.

* * * * *